(12) United States Patent
Hofmann et al.

(10) Patent No.: US 8,338,092 B2
(45) Date of Patent: Dec. 25, 2012

(54) METHOD AND APPARATUS FOR SPORE DISRUPTION AND/OR DETECTION

(75) Inventors: Oliver Hofmann, South Kensington (GB); Andreas Manz, East Molesey (GB)

(73) Assignee: Qinetiq Limited (GB)

( * ) Notice: Subject to any disclaimer, the term of this patent is extended or adjusted under 35 U.S.C. 154(b) by 801 days.

(21) Appl. No.: 10/558,966

(22) PCT Filed: Jun. 9, 2004

(86) PCT No.: PCT/GB2004/002472
§ 371 (c)(1),
(2), (4) Date: Dec. 1, 2005

(87) PCT Pub. No.: WO2004/108959
PCT Pub. Date: Dec. 16, 2004

(65) Prior Publication Data
US 2007/0026401 A1    Feb. 1, 2007

(30) Foreign Application Priority Data
Jun. 9, 2003   (GB) .................................. 0313170.3

(51) Int. Cl.
*C12Q 1/68* (2006.01)
(52) U.S. Cl. ........................................ 435/6.1
(58) Field of Classification Search .................. None
See application file for complete search history.

(56) References Cited

U.S. PATENT DOCUMENTS
3,941,670 A    3/1976  Pratt

FOREIGN PATENT DOCUMENTS
EP    1 271 609    1/2003
EP    1 284 495    2/2003

OTHER PUBLICATIONS

Warriner et al. Journal of Applied Microbiology vol. 88:678-685. 2000.*
Dhawan, et al. "Development of a laser-induced cell lysis system", Anal Bioanal Chem, pp. 421-426 (2002).
Warriner et al., "Inactivation of *Bacillus subtilis* spores on packaging surfaces by u.v. excimer laser irradiation", Journal of Applied Microbiology, pp. 678-685 (2000).
Hoover et al., "Destruction of bacterial spores by phenomennally high efficiency non-contact ulstrasonic transducers", Mat Res Innovat, pp. 291-295 (2002).
Ullom et al. "Discrimination between bacterial spore types using time-of-flight mass spectrometry and matrix-free infrared laswer desorption and ionization", Anal. Chem, pp. 2331-2337 (2001).
Ryzhov et al., "Rapid characterization of spores of *Bacillus cereus* group bacteria by matrix-assisted laser desorption-ionization time-of-flight mass spectrometry", Applied and Enviromental Microbiology, pp. 3828-3834 (2000).
Belgrader et al., "A minisonicator to rapidly disrupt bacterial spores for DNA analysis", Anal. Chem, pp. 4232-4236 (1999).
Birmingham et al., "Corona plasma discharge for rapid analysis of microorganisms by mass spectrometry", Rapid Communication in Mass Spectrometry, pp. 604-606 (1999).

* cited by examiner

*Primary Examiner* — Christopher M. Babic
(74) *Attorney, Agent, or Firm* — McDonnell Boehnen Hulbert & Berghoff LLP

(57) ABSTRACT

A method and apparatus for spore disruption and/or detection is provided. The method involves irradiating a sample with laser light, conveniently ultraviolet radiation, to disrupt any spores present and collecting any disrupted material for analysis. The disruption can involve breaking the spore open to release intrasporal DNA which is useful for fast screening and detection equipment. The disrupted material may be collected in a collection chamber which can be flushed with an extraction fluid to collect the disrupted material. The sample is preferably concentrated in a nanovial prior to being irradiated to give sample enrichment.

29 Claims, 3 Drawing Sheets

METHOD AND APPARATUS FOR SPORE DISRUPTION AND/OR DETECTION

BACKGROUND OF THE INVENTION (1) Field of the Invention

This invention relates to a method and apparatus for disrupting spores to aid subsequent analysis, especially to a method and apparatus for fast release of intrasporal DNA.

(2) Description of the Art

There is a growing need to be able to detect and identify spore forming bacteria. For example in the food industry there is a desire for rapid analysis of food stuffs to detect the presence of any bacterial spores, such as *Bacillus cereus*, before they can germinate and spoil produce and/or cause illness. Equally there is a need for rapid detection/identification of spores such as *Bacillus anthracis*.

The current gold standard for detection of spores is germination via heat activation and outgrowth. However this process takes up to 48 hours and requires skilled personnel and therefore is unsuitable for rapid identification.

More rapid tests exploit antibodies associated to the surface of the spores (exosporium) for detection. Handheld immunochromatographic tests are available but the sensitivity of such test are low.

Matrix Assisted Laser Desorption and Ionisation (MALDI) is a standard technique for transferring large biomolecules into the vapour phase for mass spectrometric analysis. MALDI has been used to detect specific biomarkers associated with the outer layers of the spores.

In a MALDI analysis the analyte of interest is mixed with a suitable matrix material and a solvent on a substrate. The solvent is then evaporated to leave the analyte co-crystallised with the matrix material. A pulsed UV laser source is then directed to irradiate the sample. The matrix material absorbs the laser light and a rapid temperature increase causes disintegration of the matrix ejecting a plume of sample. The ejection plume is input to a mass spectrometer to analyse the ionised biomolecules and hence the irradiation step is performed in a high vacuum.

The various biomarkers associated with the exosporium can then be identified. However the method is not good at discriminating between different *Bacillus* species as the origin and identity of the biomarkers may be unclear and different species may have similar biomarkers. To increase the number of released biomarkers corona plasma discharge may be used or sonication pre-treatments could be used but discrimination between species is still relatively poor.

Sonication may also be used to modify the surface of spores so as to aid subsequent detection in an immunoassay, for instance immunoassays involve the binding of an analyte to a specific antibody contained on the surface of a sensor. Detection sensitivity can be improved by modification of the surface of the species to be detected so as to improve subsequent binding to the antibodies on the biosensor.

Another method of screening for spores is to completely disrupt the spore so as to release intrasporal DNA for subsequent analysis via polymerase chain reaction (PCR) assays. For instance ultrasonication has recently been proposed to completely disrupt spores in 'Belgrader P.; Hansford D.; Kovacs G. T. A.; Venkateswaran, K; Mariella, R.; Milanovich, F.; Nasarabadi, s.; Okuzumi, m; Pourahmadi, F.; Northrup, M. A. *Analytical Chemistry* 1999, 71, 4232-4236'. However the samples can require pretreatments of up, to 90 minutes and so far the amount of intracellular DNA released has been low so the technique would not currently be sensitive enough for most applications.

SUMMARY OF THE INVENTION

It is therefore an object of the present invention to provide a method and apparatus for disrupting spores for subsequent detection which mitigates at least some of the aforementioned disadvantages.

Thus according to the present invention there is provided a method of disrupting any spores in a sample comprising the steps of irradiating a sample with laser light so as to disrupt any spores present in the sample; and collecting any disrupted material.

The method according to the present invention therefore uses laser energy to disrupt any spores present in the sample and then collects the disrupted material for subsequent analysis. Thus the method of the present invention allows very rapid disruption of any present spores for subsequent analysis—for instance screening for certain bacteria.

The method may involve enclosing the sample in a collection chamber and irradiating the sample within the collection chamber. This can provide a sealed environment for spore disruption. The method may also be arranged to irradiate the sample so as to disrupt any spores present in the sample and eject material into the collection chamber. This can allow for efficient collection of the disrupted material within the collection chamber. The collection step may comprise the step, subsequent to irradiating the sample, of flushing the sample within an extraction fluid.

Thus the present invention provides a rapid and simple means of disrupting spores in a sample. The irradiation may be sufficient to eject material into a collection chamber where it can be easily collected for subsequent analysis. However the irradiated sample will also contain disrupted material and flushing the sample with an extraction fluid will collect such material. It is therefore possible to use laser light which is intense enough to disrupt the spores but which is below the threshold for ejecting material into the vapour phase. Depending upon the material used this could have advantages as a less intense irradiation step may cause less damage to any material released from the spore.

As the material ejected into the collection chamber is collected for subsequent analysis the environment for irradiation does not need to be in vacuo. Indeed the chamber could be at atmospheric pressure and could just contain air. This removes the need for vacuum pumps etc. and means that samples can be easily collected in situ. Of course the collection chamber could, if required, be filled at least partly with another fluid other than air. It may even be possible to fill the collection chamber with a liquid to aid transfer of ejected material to an analysis chamber.

As used herein the term disruption may mean modification of the surface of the spore in a similar manner as described above with reference to sonication. In some embodiments however it is preferable to completely disrupt the spore so as to release the DNA contained within the spore. Intracellular DNA can be used to uniquely identify the particular bacterium by any known method such as PCR. Conveniently therefore the irradiation step is arranged to disrupt the spore so as to eject material from within the spore, such as DNA, into the collection chamber.

Conveniently the sample is disposed within a matrix material. Disposing the sample within a matrix material can aid in energy transfer from the laser as the matrix material can be arranged to hold any spores in a specified location and to absorb the incident radiation and undergo an explosive type decomposition to disrupt the spores. Conveniently the matrix material is chosen so that it has maximum disruptive effect but does not destroy the released material of interest. Where it is desired to release intrasporal DNA it has been found that matrix materials used in standard MALDI techniques where DNA is the sample material are advantageous, resulting in complete disruption of the spore but no damage to the released DNA.

In some cases however it may not be necessary to use a matrix material and the sample alone could be irradiated.

Conveniently the method includes the step of locating the sample on a substrate. Conveniently this involves mixing the sample, and any matrix material, with a solvent. The solvent mixture is then placed on the substrate and the solvent evaporated to leave the sample. Where a matrix material is used the sample is left co-crystallised with the matrix material.

Preferably the step of locating the sample on the substrate comprises the step of locating the sample in at least one micro-structured vial on the substrate. Locating the sample in a micro-structured vial on the substrate tends to localise the sample in one place providing inherent enrichment of the sample which can increase the sensitivity of the process. Further as the sample is located in the micro-structured vial a high power laser can be focussed just on the micro-structured vial to cause spore disruption resulting in enhanced disruption. Conveniently the sample is mixed with a solvent as discussed and applied to the micro-structured vial. Upon solvent evaporation the sample remains pinned to the micro-structured vial due to surface tension. The sample then crystallises into the vial. Given that the solvent-sample droplet will be larger than the micro-structured vial the method therefore enriches the sample in the micro-structured vial. Repeating the process with more drops provides yet further enrichment of sample.

The at least one micro-structured vial may have a volume of less than 100 nL or less than 10 nl or less than 1 nl or less than 0.1 nL.

Preferably the method involves locating samples in a plurality of micro-structured vial on the substrate. The plurality of micro-structured vial may be arranged as an array. In use each micro-structured vial may be arranged to be co-located with a separate collection chamber thereby allowing several samples of material to be disrupted and collected separately, say by sequential irradiation by a laser. Alternatively a parallel illumination arrangement could be used if desired. This allows a plurality of disrupted samples to be collected. In this way the same assay may be performed several times to verify results and reduce susceptibility to error. Additionally or alternatively more than one assay may be performed on the material so as to improve detection and identification.

Preferably the wavelength of illuminating radiation is substantially matched to the absorption maximum of the chosen matrix material, when used. In other words the skilled person will be aware of the absorption maximum for the chosen matrix material, i.e. the wavelength at which radiation is most strongly absorbed, and therefore the wavelength of illuminating radiation is preferably chosen to be at or near to this maximum. As mentioned above the matrix material may be selected for low fragmentation of intrasporal DNA samples but could be also chosen to enable low fragmentation of spore coat proteins where these are the analyte of interest for the chosen detection method. This would be of interest if one were to use uniquely identifiable proteins within the outer-exosporium layer of the spore for identification purposes as an alternative to DNA analysis using PCR. Conveniently the wavelength of illumination is within the ultraviolet range, for instance within the range 400-10 nm.

Preferably the sample is illuminated with pulses of laser radiation, having a duration in the range 1 ns to 100 ns. Conveniently relatively low power laser illumination is used with power in the region of 75 kW peak power. This gives pulse energies of 300 microjoules in energy and at a repetition rate of 35 Hz corresponds to an average power or 6 mW.

The method may also comprise an initial step of washing the sample prior to irradiating with laser light so as to remove low molecular weight acid soluble proteins associated with the outer spore layers, this could render the spore more susceptible to disruption by irradiation, especially irradiation with UV radiation. Spores can be coated with proteins which protect the spore from radiation such as UV radiation. By pre-treating the sample to remove or reduce such protective proteins the power and/or duration of laser illumination required to disrupt the spore can be reduced as compared to illuminating a sample without a pre-treatment. This can allow shorter illumination times which may be useful for ultra rapid detection systems. Conveniently the sample is washed with an acidic aqeous based solvent to release and remove at least some of the protective proteins. This could be achieved in a sample pre-treatment step just prior to the laser irradiation.

The step of enclosing the sample within a collection chamber conveniently comprises the step of securing a collection plate to the substrate, the substrate and collection plate defining a cavity within which the sample is located. By securing a collection plate to the substrate when the sample is illuminated the ejected material may be ejected as a plume and will be deposited on the collection plate. The collected material could then be used in a detection step as will be described later. Conveniently the collection plate has a microchannel formed therein and the microchannel at least partly forms the cavity of the collection chamber. Conveniently the microchannel is configured so that it may be used as part of a microfluidic circuit—in this way the collection plate may be removed from the substrate and used as part of a microfluidic circuit to aid subsequent detection steps. In some embodiments the substrate and collection plate could together be used as part of a microfluidic circuit.

The method may involve filling the collection chamber at least partly with an extraction fluid, which may be water for instance, in order to better collect the ejected material. With the collection chamber at least partly filled with an extraction fluid the ejected material is not only more efficiently collected but the extraction fluid can be flushed through without needing to remove the original sample which reduces the possibility of contamination. When a solid matrix material is used it may be necessary to keep an air gap between the extraction fluid and the sample/matrix so as to prevent the sample dissolving. However liquid matrix materials may be used in which case a liquid-liquid interface needs to be maintained. Parts of the collection chamber may have surface treatments to keep the extraction fluid from mixing with the sample.

As mentioned the disrupted sample material can then be subjected to any of a number of assays to detect and/or identify certain bacteria in spore form. Therefore in a second aspect of the present invention there is provided a method for performing a test for the presence of certain spore forming bacteria in a sample comprising the steps of treating the sample so as to disrupt any spores present by applying the method of the first aspect of the invention and performing a test on the collected ejected material to determine the presence or otherwise of a known bacteria.

Advantageously the collected material may be intrasporal DNA in which case the step of testing the collected material may involve performing a PCR based assay. As mentioned PCR assays on intrasporal DNA can uniquely identify the bacteria or detect the presence of particular bacteria. PCR analysis is a well known and relatively quick analysis technique. The disruption method of the present invention is a very quick and efficient way of obtaining undamaged intrasporal DNA with relatively simple equipment. Therefore the method according to the second aspect of the invention offers an extremely quick and simple analysis equipment which can offer in situ analysis of material to determine the presence or otherwise of particular bacterial agents.

Where the ejected sample material is collected in a collection plate having a microfluidic channel the detection method may involve the first step of disrupting the sample according to the first aspect of the invention, removing the collection plate from the substrate and introducing it to a microfluidic circuit and performing the required assay in the microfluidic circuit.

As mentioned the method according to the first two aspects of the invention provides for very fast spore disruption. The irradiation step may last for one second or less.

In a third aspect of the invention there is provided an apparatus for disrupting spores located on a substrate comprising a collection plate releasably securable to the substrate to define a collection chamber and a laser apparatus arranged to illuminate a sample within the collection chamber so as to disrupt any spores present in the. The apparatus according to the third aspect of the invention has all the advantages described above with reference to the first two aspects of the invention. It provides a rapid and simple method of disrupting spores to aid subsequent detection or to release intrasporal material for use in subsequent assays.

The laser may be arranged to disrupt any spores present and eject material in the collection chamber. Conveniently the laser apparatus comprises an ultraviolet laser. The laser preferably has an emission wavelength matched to the excitation region of the absorbing matrix material, ideally at the maximum absorption wavelength. Preferably the laser is a pulsed laser.

Preferably the substrate has at least one micro-structured vial located therein to hold sample material. As mentioned above use of a micro-structured vial can usefully contain sample material for irradiation and can also serve to enrich the sample giving enhanced sensitivity.

Preferably the collection chamber comprises a microchannel formed in the collection plate and the collection plate can be used as part of a microfluidic circuit.

The present invention could be usefully employed as a kit for detection of certain bacterial agents. Therefore in a fourth aspect of the present invention there is provided a kit for screening for the presence or otherwise of spore forming bacteria comprising a substrate having at least one micro-structured vial for holding a sample and a collection plate relesably securable to the substrate, the substrate and collection plate defining a collection chamber adapted, in use, to collect material ejected from a sample disposed in the micro-structured vial upon illumination with a laser. In use sample material is mixed with a solvent and deposited on the substrate over the micro-structured vial. The solvent then evaporates and surface tension keeps the sample material at the micro-structured vial. Generally a matrix material is also mixed with the solvent and the sample and after the solvent has evaporated the matrix material and sample are co-crystallised in the micro-structured vial. The kit therefore preferably comprises a solvent and possibly a matrix material.

The kit may also comprise means for illuminating a sample disposed in the collection chamber with laser light so as to disrupt any spores in the sample and eject material into the collection chamber.

Preferably the kit also comprises a test means for performing an assay on the collected material. This test means preferably comprises a microfluidic circuit which the collection plate can be releasably secured to, either together with the substrate or having been detached therefrom. The test means may perform a PCR based assay on released intrasporal DNA. The kit according to the present invention therefore provides a simple and easy to use screening kit which can be used in situ and yield rapid results for detection or otherwise of known agents.

Part of the reason that the present invention is so useful is the benefit gained through enriching the sample in a micro-structured vial prior to irradiation. Therefore according to a fifth aspect of the invention there is provided a method of enriching a sample of material comprising the steps of dissolving the sample in a solvent, placing a droplet of solution on a micro-structured vial in a substrate and evaporating the solvent so as to crystallise the sample in the micro-structured vial. It should be noted that the terms dissolving and solution should be read broadly. Depending on the analyte of interest the sample may not actually be dissolve in the solution but may be suspended in a suspension. For example spore forming bacteria will not be dissolved as such but will be held in suspension. However some analytes may actually dissolve. Therefore throughout this specification the terms dissolve and suspend and solution and suspension should be read interchangeably depending upon the analyte of interest. Also it should be noted that the enrichment process described with regard to the fifth aspect of the invention is applicable to a wide range of possible analytes and is not limited to spore forming bacteria. A similar enrichment effect would be achieved with a range of low abundance materials where the surface chemistry of the target plate and micro-structured vial are such so as to draw the sample into the vial. For instance when the substrate is PDMS the method would work well with analytes that are hydrophobic in nature, for instance peptides/proteins.

Preferably the method involves adding a matrix material to the solution so that the sample co-crystallises with the matrix material in the micro-structured vial. This allows a large droplet of sample material to be crystallised in the micro-structured vial resulting in an enriched sample as compared to that had a flat substrate been used. The enriched sample may then be irradiated in one go by a high power laser with a narrow beam cross section resulting in efficient energy transfer and maximising the amount of disrupted spore material that may be collected.

The method of enrichment may also involve the step of repeatedly applying a drop of solvent/material mix onto the micro-structured vial so as to further enrich the sample in the micro-structured vial. Preferably the sample is enriched by a factor of 10 or greater, 100 or greater, 1000 or greater or 10,000 or greater.

DESCRIPTION OF THE FIGURES

The invention will now be described by way of example only with respect to the following drawings of which.

DETAILED DESCRIPTION OF THE INVENTION

Figure 1:
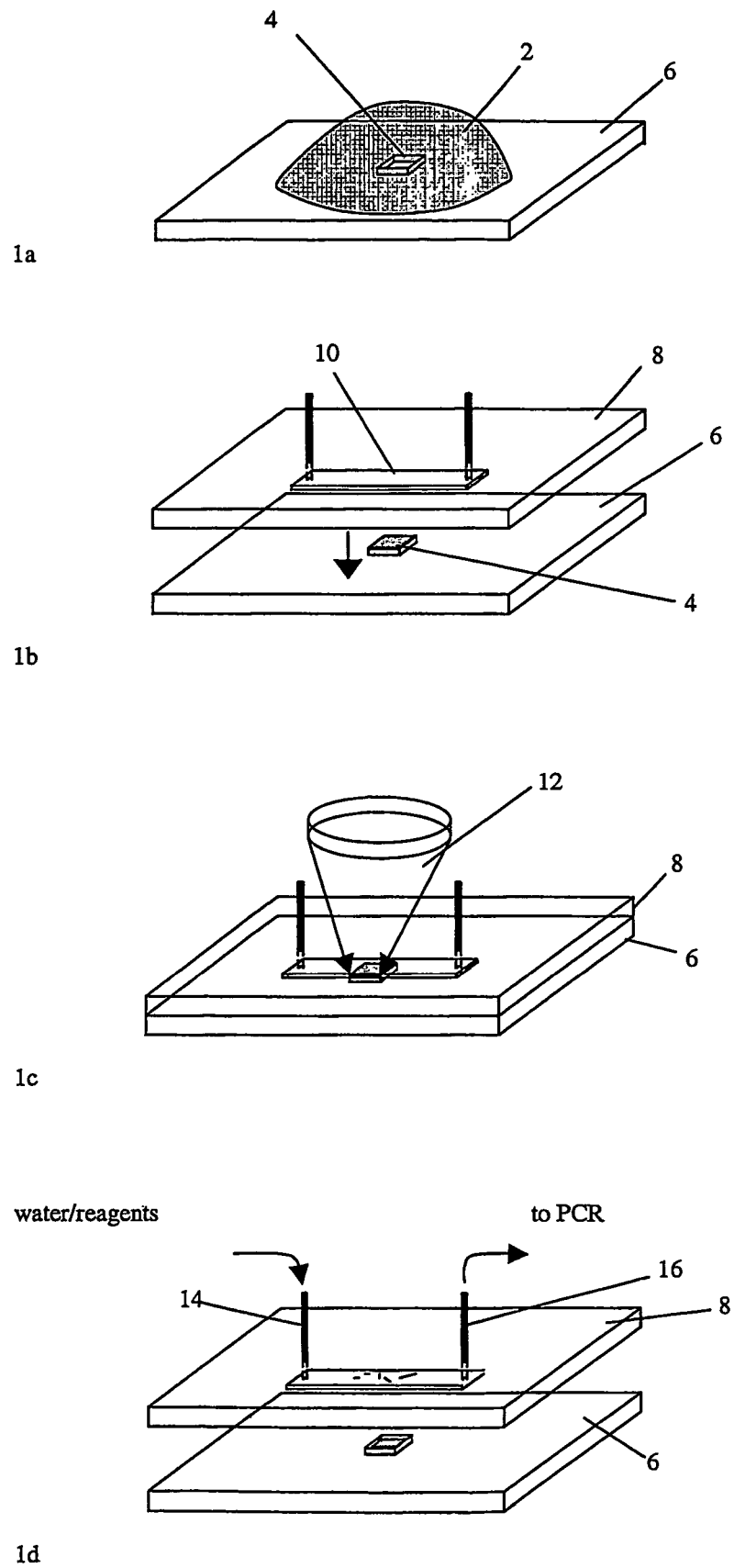
FIG. 1 shows a schematic of the steps of the method of the present invention.

Referring to FIG. 1 schematically is shown a laser based spore enrichment and disruption process with integrated extraction of desorbed intrasporal content in a microchip format at atmospheric pressure. Amplification and identification of any released DNA may then be performed in a second step by PCR. A sample containing, or thought to contain, spores is first mixed with a laser light absorbing matrix and a solvent and a drop 2 of the mixture is applied onto a microstructured vial such as nanovial 4 in an elastomer plate 6—see FIG. 1a. Upon solvent evaporation the drop remains pinned to the nanovial 4 due to surface effects and eventually crystallises into the nanovial. This allows for drop volumes much larger than the nanovial volume to be applied, resulting in sample enrichment in the vial. A second elastomer plate which comprises a collection plate 8 with a microstructured channel 10 is then attached to the sample zone plate 6—FIG. 1b. Referring now to FIG. 1c, upon laser illumination 12 of the sample zone through the collection plate 8, the explosive disintegration of the matrix breaks open the protective spore layers. Simultaneously, released intrasporal content is ejected in a plume and deposited onto the inner walls of the microchannel 10 in the collection plate 8. Since attachment of the two plates is adhesion based, the top plate 8 can readily be removed after illumination. Any released intrasporal DNA is then recovered by flushing the channel in the top plate 8 with water and the collected volume is subjected to PCR—FIG. 1*d*.

The process described above allows ultrafast spore disruption in the second to sub-second range. Furthermore, the sample enrichment and amplification in the PCR step yields high sensitivity. It should be noted however that other assays than PCR based assays could equally be applied and that the disruption process may be designed to modify the surface of the spores for subsequent analysis rather than break open the outer spore layers.

The first step, as mentioned, is to mix the sample with a suitable matrix material and a solvent. The choice of matrix material will depend upon the desired result but matrix materials known for Matrix Assisted Laser Desorption and Ionisation (MALDI) may be appropriate. Where it is wished to break open the spore to release intrasporal DNA a matrix known for MALDI DNA analysis may be used. For DNA analysis the most commonly used matrix materials are 2,4,6-trihydroxyacetophenone (THAP), 6-aza-2-thiothymine (ATT) and 3-hydroxypicolinic acid (3-HPA). It should be noted however that when used in a MALDI apparatus it is necessary that the resultant material be ionised. This is not necessary in the present invention and hence the choice of matrix material is less constrained. In principle any matrix which is soluble in an aqueous medium and absorbs highly at the wavelength of operation will be sufficient. 3-HPA was used in tests as a suitable candidate based on its solubility in water and comparatively low fragmentation effects on target DNA. The laser source used was a nitrogen laser with a 4 ns pulsed output at 337 nm. The emission wavelength of 337 nm is strongly absorbed by 3-HPA. The skilled person will appreciate however that materials which could equally be used for a matrix which might have higher absorption maxima and/or lower fragmentation effects on DNA samples or may be designed to release other analytes and absorb at different wavelengths suitable for excitation using other illumination sources.

The energy density of the illuminating radiation will vary depending on the optical set-up used for illumination. The skilled person will be aware of various optical arrangements that could be used. For instance optic fibre coupling or use of appropriate lenses (open beam configuration). A range of output energies of between 0.4 microJoule (equivalent to 0.04 mJ/cm2, which is below the threshold energy density of ~10 mJ/cm2 required for desorption and plume ejection—obtained using the optic fibre set-up) and 68 microjoules (energy density of 170 mJ/cm2, obtained using the open beam configuration) were achieved.

It should be noted that prior art MALDI schemes for analysis of spores have not resulted in complete spore disruption and have concentrated on releasing ionised biomarkers from the exosporium. As such the matrix materials mentioned above have not previously been regarded as suitable for use with spores in a MALDI analysis.

It is also noted that spores contain dipicolinic acid in the outer layers and as such a matrix material might not be required in all embodiments and absorption of laser light by the spores themselves may be sufficient to cause disruption.

Solvent choice is governed by the need to maintain analyte suspension and promote partitioning of the analyte into the matrix crystals during drying of the analyte/matrix mix. For DNA analysis the solvent of choice is water (both DNA and the above mentioned matrices are water soluble). To reduce the drying time and to get a more uniform and dense crystal deposit, more volatile organic solvents such as acetone or acetonitrile can be added. However, the reduced surface tension of the resulting solvent systems can adversely affect the confinement of the evaporating drop into the microstructured sample vial 4 (high surface tension keeps the evaporating drop pinned to the vial, "corralling effect"). Sample spot confinement is important to get a well defined target for the laser beam 12 and as will be described later is important in a two phase flow system for extraction of potentially released spore DNA.

Various experiments were conducted on solvent mixtures and concentrations to determine the optimum conditions for application and evaporation of 0.1 μL of sample/matrix mix into the microstructured sample vials. Reproducible, near-perfect confinement and dense, uniform deposits were obtained for 10 mg/mL 3-HPA in 40% acetonitrile/60% aqueous. Further sample enrichment was attempted through multiple application/evaporation of droplets and through increasing the applied volume. While the former approach is hampered by deposits being redissolved the latter approach looks promising for microlitre volumes. However, the matrix concentration has to be adjusted to the applied volume. Also there appears to be a limit to the sample concentration that can be analysed in this way. For proper crystal formation the matrix always has to be in around 1000× molar excess with respect to the analyte.

The sample plate and collection plate may be fabricated from polydimethylsiloxane (PDMS) by moulding from a photoresist master. However other methods may be more appropriate and the skilled person would know of a range of methods that could be applied to fabricate the plates.

The microfluidic layout of the collection plate may vary depending upon the required use as will the dimensions. By way of example only the main channel may be in the region of 5 mm long. The width of the main channel may vary between 600-1000 μm, but might be more if an array of nanovials is used. The depth may be approximately 10 μm to minimise the extraction volume (main channel: 30-50 nL). The sample spot size, and hence the size of the nanovial, is limited by the minimum diameter of the laser beam. Using a commercially available nitrogen laser with a coupler and suitable fibre optics and post fibre focussing optics a beam diameter of the order of 200 μm may be achieved with a power density of approximately 8 mJ $cm^{-2}$ (with a coupling loss of approximately 90%). Therefore sample vials with dimensions ranging from 200-500 μm were designed (volume: 0.4-1 nL).

Sample vial arrays should allow multiple shots without need for repositioning of the microfluidic chip.

The exact design of chip will depend upon the means by which the ejected material is to be collected. It is possible to use a solid or liquid matrix material with air in the rest of the collection chamber and collect material on the inside walls of the chamber. In such an embodiment the sample zone and extraction liquid are arranged in a vertical arrangement, as shown in FIG. 1, to exploit best directionality of the plume (normal to the surface). After irradiation of the sample material will have been deposited on the walls of the channel 10 in plate 8. Collection plate 8 may then be detached from sample plate 6 and have another flat plate attached as a seal (not shown). Water may then be fed into the channel through inlet 14 and out through outlet 16 to flush the deposited material out where it may be used in a subsequent analysis.

As will be explained later however there are a variety of geometries for the collection chamber and it may not be necessary to separate the substrate from the collection chamber to flush through with extraction fluid. Indeed it may be wished to collect the material from the nanovial 4 in the extraction fluid as this will also contain disrupted material. In some embodiments the laser illumination is sufficient to disrupt the spores but is not sufficient to eject any material out of the nanovial, i.e. no material is volatilized. In this case all the disrupted material will be left in the nanovial following illumination. Illuminating below the threshold required to eject material into the vapour phase can be advantageous where the material of interest, for instance intracellular DNA, is relatively fragile and could be damaged by intense irradiation. Prior art MALDI techniques all work on material ionised in the vapour phase and so illumination has to be above the threshold to eject material into the vapour phase.

In some embodiments then there is no need for a collection plate and the sample and any matrix material may be illuminated directly with disrupted material being left in the nanovial for collection.

The method may also involve a pre-treatment step of washing the sample thought to contain spores to remove or reduce any radiation protective proteins, so called low molecular weight acid soluble proteins from the spore outer layers. As will be understood by one skilled in the art the spore layer may contain various proteins which act to protect the spore from radiation damage or disruption, such as UV radiation. When irradiated these proteins in the layer/s may serve to protect the spore. By pre-washing the sample with a suitable treatment, such as an acidic aqueous based solvent, the amount of protective proteins on the spore layer/s can be reduced. This can reduce the power and/or duration of radiation exposure needed to disrupt the spore. When the method is used in a ultra rapid detection system for identifying dangerous pathogenic organisms speed of detection is key and so a reduced illumination time may be beneficial. The skilled person would be aware of possible low molecular weight protective proteins for the spores of interest and suitable treatments to pre-wash the sample with.

Figure 2A:
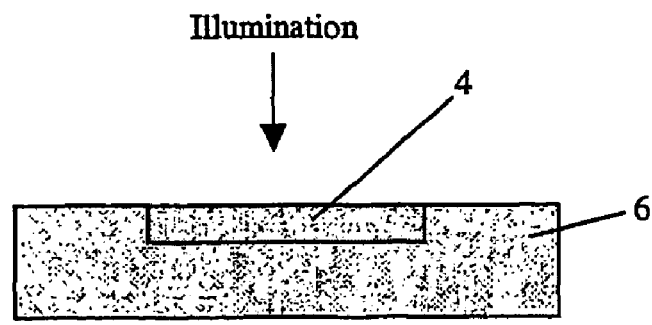
FIG. 2 shows two alternative layouts for the collection chamber.

FIG. 2 shows a range of possible geometries. FIG. 2a shows the situation where spores alone are irradiated in a nanovial with the disrupted material being left in the nanovial for collection. The same arrangement would equally apply were the spore mixed with a matrix material which may be solid or liquid.

Where a liquid matrix material is used, or the spores are disposed in water, and it is desired to collect ejected material in a collection chamber an arrangement similar to that shown with respect to FIG. 1 may be used.

Figure 2B:
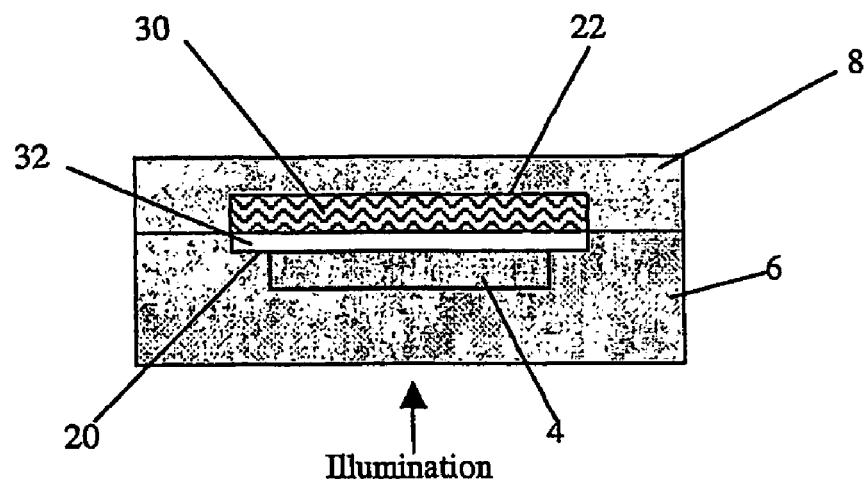

In some embodiments though it may be better to have the material captured in liquid in the collection chamber. Where a solid matrix material is used however it is necessary to keep an air interface between the crystallised sample/material mix and any extraction liquid to prevent the sample/matrix from re-suspending. FIG. 2b shows a layout that may be used when the matrix used is a solid. In this case the PDMS sample plate 6 would comprise a channel 20 with lower level sample nanovials 4. This sample plate 6 would be placed below a PDMS collection plate 8 comprising a second channel 22. The PDMS material in the second plate 8 is plasma-treated to improve its hydrophilicity (or another treatment such as silanisation could be employed). Introducing the aqueous liquid phase extraction fluid 30 into the assembled microchip would then result in selective filling of the channel in the collection plate due to the higher hydrophilicity. This should leave the channel 20 on top of the sample vial filled with air 32, resulting in an air-liquid interface. Illumination of the sample zone 4 through the sample plate could then be used to generate a plume directed towards the liquid extraction phase. This should greatly enhance the extraction yield. Alternatively using a reflection geometry the sample could be illuminated through the collection plate 8.

Figure 2C:
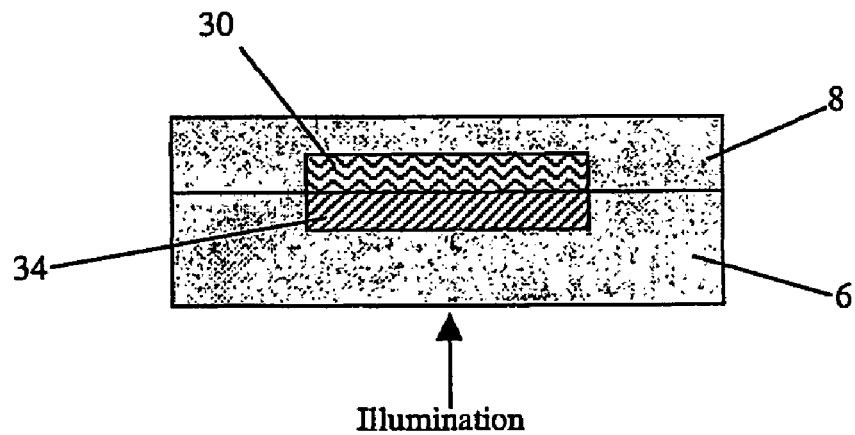

In another embodiment, shown in FIG. 2c, a liquid phase UV matrix 34 could be employed in a liquid/liquid configuration. Again illumination would be in a transmission geometry through the UV matrix. Such an arrangement could be implemented in a parallel or layered flow configuration (illumination from side or top, respectively).

Test Results

Using the apparatus shown in FIG. 1 experiments were performed to test for spore disruption. 0.1 µL of $10^8$ cfu/mL *Bacillus globigii* spores was mixed 1:1 with 10 mg/mL 3-HPA matrix in 40 v/v-% ACN/60% water and was applied onto a 200×200 µm nanovial with a 20 µm depth molded in Polydimethylsiloxane (PDMS). Upon solvent evaporation this resulted in a 100-fold enrichment with ~10,000 spores in the vial. In a first test experiment the PDMS flowcell was not attached and the zone was directly illuminated for 1 second at 30 Hz with a 6 mW 337 nm nitrogen laser via fibre optics (output ~50 µJ/cm$^2$). Desorption was not observed and the sample zone was redissolved in 1 µL sterile water and subjected to PCR. It should be noted that the spores were pre-treated with chloros (sodium hypochlorite) prior to illumination to remove any extrasporal DNA.

Figure 3A:
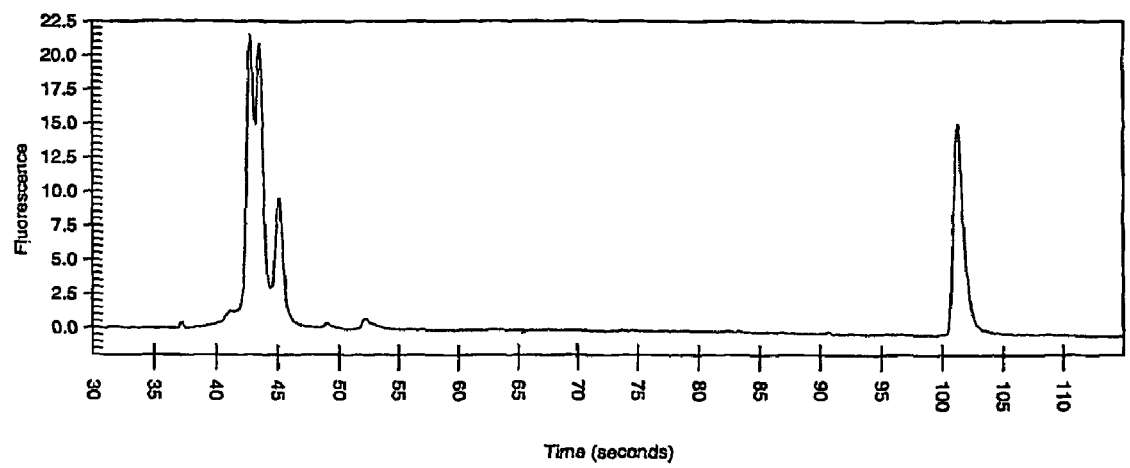
FIG. 3 shows PCR results for a) a control sample of spores and b) a sample of spores after being irradiated according to the present invention for 1 second.
Figure 3B:
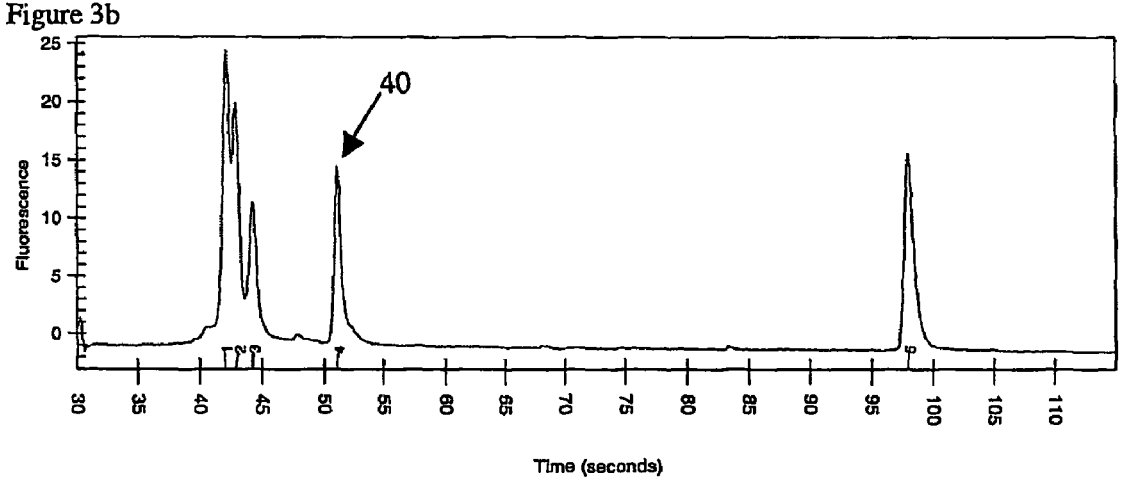

First a negative control group of untreated spores was subjected to the PCR treatment. The results are shown in FIG. 3a. Then a sample of spores that had been illuminated for 1 second was analysed and the results are shown in FIG. 3b. The PCR product (78 bp) is highlighted 40.

The results clearly show that release of intrasporal DNA occurred. Electron micrographs of the illuminated zone confirmed spore damage.

In order to also induce desorption the optical set-up was changed to an open beam configuration with focusing optics yielding an output of ~170 mJ/cm$^2$. Experiments revealed complete desorption of the sample zone within seconds under atmospheric pressure to enable recovery of intrasporal content with the geometries described above.

The invention claimed is:
1. A method of detecting spores in a sample comprising the steps of:
irradiating a sample with laser light so as to disrupt any spores present in the sample, thereby releasing material from within the spores;
collecting the released material; and subsequently analysing the released intrasporal material so as to determine the presence or otherwise of bacteria.

2. A method as claimed in claim 1 wherein the method includes the step of enclosing the sample within a collection chamber and the sample is irradiated within the collection chamber.

3. A method as claimed in claim 1 wherein the step of irradiating the sample involve irradiating the sample sufficiently so as to disrupt any spores present in the sample and eject material into the collection chamber.

4. A method as claimed in claim 3 wherein any ejected material is collected within the collection chamber.

5. A method as claimed in claim 1 wherein the step of collecting any disrupted material involves the step, subsequent to irradiating the sample, of flushing the sample with an extraction fluid.

6. A method as claimed in claim 1 wherein the step of irradiating the sample is performed at substantially atmospheric pressure.

7. A method as claimed in claim 1 wherein the method includes the step of disposing the sample within a matrix material prior to irradiation.

8. A method as claimed in claim 1 wherein the method comprises the initial step of locating the sample on a substrate.

9. A method as claimed in claim 8 wherein the step of locating the sample on a substrate comprises disposing the sample in a solvent, placing the solvent-sample mixture on the substrate and evaporating the solvent.

10. A method as claimed in claim 8 wherein the step of locating the sample on the substrate comprises the step of locating the sample in at least one micro-structured vial on the substrate.

11. A method as claimed in claim 10 wherein the step of locating the sample in at least one micro-structured vial enriches the sample in the micro-structured vial.

12. A method as claimed in claim 10 wherein the substrate comprises a plurality of micro-structured vials and the method involves the step of locating a sample in each micro-structured vial.

13. A method as claimed in claim 12 wherein the method involves enclosing each micro-structured vial in a separate collection chamber and separately irradiating each sample in a micro-structured vial.

14. A method as claimed in claim 2 wherein the method includes an initial step of locating the sample on a substrate and wherein the step of enclosing the sample within a collection chamber comprises the step of securing a collection plate to the substrate.

15. A method as claimed in claim 14 wherein the collection plate has a microchannel formed therein, the microchannel forming at least part of the collection chamber.

16. A method as claimed in claim 15 wherein the microchannel is configured so that it can be used as part of a microfluidic circuit.

17. A method as claimed in claim 2 wherein the collection chamber is at least partly filled with an extraction fluid to collect any disrupted material.

18. A method according to claim 1 further comprising the step of performing a test on the collected material to determine the presence or otherwise of bacteria.

19. A method according to claim 18 wherein the collected material is intrasporal DNA and the test to determine the presence or otherwise of known bacteria comprises a PCR based assay.

20. A method according to claim 18 wherein the method includes an initial step of locating the sample on a substrate and wherein the step of enclosing the sample within a collection chamber comprises the step of securing a collection plate to the substrate and wherein the step of performing a test on the collected material involves removing the collection plate from the substrate, introducing it into a microfluidic circuit and performing the test in a microfluidic circuit.

21. A method as claimed in claim 1 wherein the step of irradiating the sample is performed for a second or less.

22. A method as claimed in claim 1 wherein the irradiating radiation has a wavelength in the ultraviolet range.

23. A method as claimed in claim 1 wherein the irradiating radiation is pulsed radiation, each pulse having a duration of between 1 ns and 100 ns.

24. A method as claimed in claim 1 wherein the released material is intrasporal DNA.

25. A method as claimed in claim 1 comprising the additional step of performing an assay on the released material.

26. A method as claimed in claim 25 wherein the released material is DNA and the assay is a PCR based assay.

27. A method of detecting spores in a sample comprising the steps of:
   irradiating a sample with a laser light so as to modify the surface of any spores present in the sample;
   collecting the modified spores; and
   analyzing the collected spores by an immunoassay.

28. A method of detecting spores in a sample comprising the steps of:
   irradiating a sample with laser light at substantially atmospheric pressure so as to disrupt any spores present in the sample, thereby releasing material from within the spores;
   collecting the released material; and
   subsequently analysing the released material, wherein the laser light has an output energy in excess of about 10 $mJ/cm^2$ so as to induce desorption of the disrupted sample.

29. A method according to claim 28, wherein the sample is located on a sample plate and the released material is ejected onto a collection plate.

* * * * *